United States Patent [19]

Cheminal et al.

[11] Patent Number: 4,579,974

[45] Date of Patent: Apr. 1, 1986

[54] CATALYTIC PROCESS FOR THE PREPARATION OF HEXAFLUOROACETONE

[75] Inventors: Bernard Cheminal, Lyons; Henri Mathais, Saint Didier Au Mont D'or, both of France

[73] Assignee: ATOCHEM, Courbevoie, France

[21] Appl. No.: 679,185

[22] Filed: Dec. 7, 1984

[30] Foreign Application Priority Data

Dec. 13, 1983 [FR] France ................. 83 19915

[51] Int. Cl.$^4$ ............................................. C07C 45/63
[52] U.S. Cl. ..................................... 568/394; 568/393
[58] Field of Search .................. 568/394, 393, 419

[56] References Cited

U.S. PATENT DOCUMENTS

| | | | |
|---|---|---|---|
| 3,257,457 | 6/1966 | Anello et al. | 568/394 |
| 3,381,044 | 4/1968 | Wiedemann et al. | 568/394 |
| 3,787,489 | 1/1974 | Anonini et al. | 568/394 |
| 3,803,241 | 4/1974 | Stolkin et al. | 568/394 |
| 3,804,778 | 4/1974 | Salindres | 568/394 |
| 3,978,145 | 8/1976 | Knaak | 568/394 |

FOREIGN PATENT DOCUMENTS 1452159 4/1966 France ................. 568/394

OTHER PUBLICATIONS

Wang, Chem. Abst., vol. 97, #916695 (1982).

*Primary Examiner*—James H. Reamer
*Attorney, Agent, or Firm*—Beveridge, DeGrandi & Weilacher

[57] ABSTRACT

Disclosed is a continuous catalytic process for the preparation of hexafluoroacetone comprising reacting in a first fluorination step a mixture of hydrofluoric acid and a chlorofluoroacetones recyclate, then in a second fluorination step, a mixture containing the effluent issuing from the first step and fresh hexachlorofluoroacetone, on a catalyst comprising gamma alumina impregnated with chromium sesquioxide $Cr_2O_3$ in an amount of 1.5 to 4 atoms of chromium per liter of alumina and activated between 300° C. and 400° C. by means of a mixture of hydrofluoric acid and 1,1,2-trichloro-1,2,2-trifluoro-ethane.

12 Claims, 1 Drawing Figure

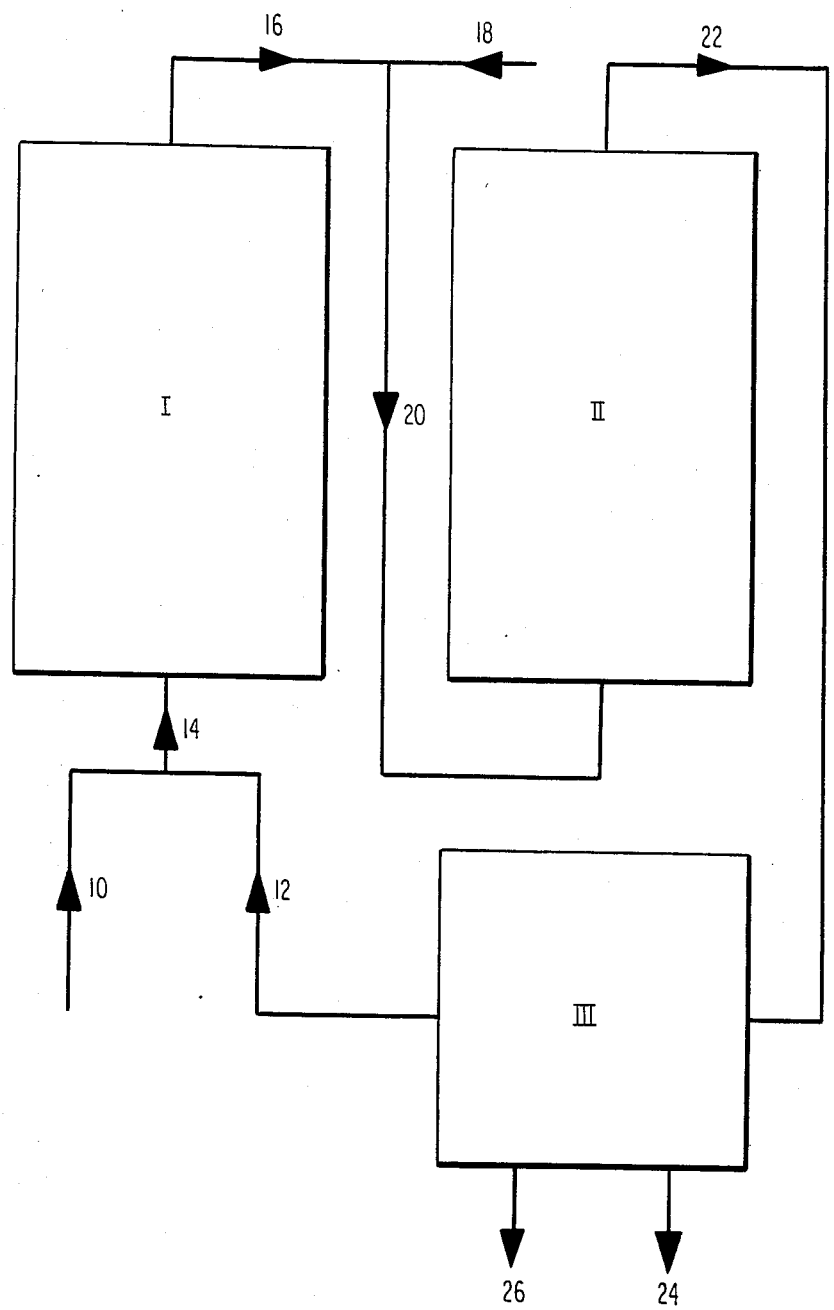

CATALYTIC PROCESS FOR THE PREPARATION OF HEXAFLUOROACETONE

The present invention relates to a continuous catalytic process for the preparation of hexafluoroacetone through fluorination of hexachloroacetone in the gaseous phase by anhydrous hydrofluoric acid.

The preparation, through the route specified hereinabove, of hexafluoroacetone as well as, moreover, of perfluorinated functional components in general from corresponding perchlorated compounds, is very difficult to carry out.

The difficulties encountered when utilizing known processes are set out in French Patent No. 2,135,474: "The state of the art shows that it is difficult to obtain simultaneously a complete perfluorination of the perchlorated compounds in a single passage of the reactants in the vapor phase fluorination zone, a suitable yield and a minimal loss of useful matter due to the parasitory decomposition reactions into non-utilizable compounds".

It is known, in fact, that when the temperature at which a fluorination is performed, by a single passage of the reactants on the catalyst, is relatively low, i.e. equal to or lower than 250° C., the perfluorinated compound can only be obtained with a clearly insufficient yield and productivity. Conducting the fluorination in multiple successive and alternate steps of separation and fluorination of the insufficiently fluorinated compounds can increase the yield of the required perfluorinated product, but the productivity nevertheless remains extremely low.

When the fluorination reaction is carried out at a high temperature, i.e. at least 300° C., the parasitory reactions rapidly bring about an excessive degradation of the products and do not permit any economic benefit from the productivity increase According to the process described in French Patent No. 2,135,474, the perfluorinated compound involved is obtained in a single passage of the reactants on the catalyst only by conducting the fluorination in three successive reaction zones that are distinct from one another, the temperature of each of the two latter reaction zones being controlled at a temperature at least 10° C. higher than that of the temperature of the immediately preceding reaction zone. Such a procedure requires a complex, delicate and expensive operation.

French Patent No. 2,135,473 discloses and claims a process adapted to the utilization of a particular catalyst comprising two non-stoichiometric inorganic compounds, one based on chromium and the other on nickel. The use of such a catalyst unfortunately leads to excessive degradation of the organic molecules corresponding, per mole, to more than 7% of the engaged hexachloroacetone.

The process according to the present invention allows one to achieve a high conversion of the hexachloroacetone, a suitable productivity and substantially negligible degradation of the organic molecules by operating at high temperature and in only two fluorination steps.

The invention is characterized by the use of a catalyst comprising a gamma alumina impregnated with chromium sesquioxide $Cr_2O_3$ in a quantity of from 1.5 to 4 and preferably about 2.5 atoms of chromium per liter of alumina and activated at a temperature between 300° C. and 400° C. by means of a mixture of hydrofluoric acid and 1,1,2-trichloro-1,2,2-trifluoro-ethane, in two fluorination steps in the gaseous phase, the first fluorination step comprising reacting at a temperature between 330° C. and 370° C., a mixture of hydrofluoric acid and recycled products comprising chlorofluoroacetones, the second fluorination step comprising reacting at a temperature between 280° C. and 320° C. a gaseous mixture comprising the gaseous effluent issuing from the first fluorination step and fresh hexachloroacetone in an amount whereby the ratio of the number of moles of hydrofluoric acid introduced into the first fluorination step to the number of halogenoacetone moles introduced into the second fluorination step is between 3:1 and 5:1, the hexafluoroacetone produced being recovered from the gaseous effluent issuing from the second fluorination step and the other or remaining halogenoacetones being recycled to the first fluorination step.

In the process according to the invention, impregnation of the alumina is accomplished by known means, such as the simultaneous and separate feeding, under vacuum, into a reactor maintained in rotation and containing the alumina, of a chromic anhydride $CrO_3$ aqueous solution, on the one hand, and of methanol, on the other hand, followed by drying the product obtained, in a fixed or fluid bed, at a temperature generally close to 150° C. in an inert gas stream such as a nitrogen stream.

Reduction of the hexavalent chromium into trivalent chromium can be carried out by using a reducing compound other than methanol, for example another alcohol, such as ethanol, or hydrazine. Activation of the catalyst is accomplished, for example, by passage of a mixture of hydrofluoric acid and 1,1,2-trichloro-1,2,2-trifluoro-ethane on the dried catalyst, preferably first at 300° C. or 350° C., thereafter at 400° C. The molar ratio of hydrofluoric acid to 1,1,2-trichloro-1,2,2-trifluoro-ethane may vary from 0.5:1 to 2:1, but it is preferably equal to about 1:1.

The absolute pressure at which both the first and second fluorination steps are generally carried out is about 1 bar. The flow-rate of the gaseous reactants on the catalyst, in both the first and second fluorination steps, is generally between 150 and 200 Nl/h/kg of catalyst.

The drawing is a schematic representation of the process according to the invention:

The mixture containing hydrofluoric acid brought by pipe 10 and the recycled products brought by pipe 12 passes through line 14 into reactor I that contains the catalyst and where the first fluorination step in the gaseous phase is carried out. To the gaseous effluent issuing from the reactor I through pipe 16 is added fresh gaseous hexachloroacetone brought by line 18 and the mixture thus obtained passes through pipe 20 into reactor II in which the second fluorination step is carried out. This second reactor contains the same catalyst as that in the first reactor.

The gaseous effluent issuing from reactor II through line 22 is treated in a manner known to those skilled in the art in a separation unit III from which issues, through pipe 24, the hexafluoroacetone and, through line 12, the products recycled to the first fluorination step. The unconverted hydrofluoric acid issuing through line 26 is advantageously recycled to the process.

The following non-limitative example illustrates the process according to the invention.

EXAMPLE

A gaseous mixture containing anhydrous hydrofluoric acid and a recyclate containing chlorofluoroacetones in a molar ratio of 1 mole of hydrofluoric acid to 0.13 mole chlorofluoroacetones, was introduced at a rate of 173 Nl/h/kg of catalyst contained in a first fluorination reactor of 40 mm diameter, and operating at 365° C. The catalyst was prepared and activated prior to use in the following manner:

A spherical reactor maintained in rotation and under vacuum, containing 0.4 l of alumina commercialized by the Harshaw company under reference Al III 73 E, the principal characteristics of which are:
presentation: extruded at about 0.8 mm diameter
$SiO_2$ content: 0.13%
total specific surface: 161 $m^2/g$
average pore radius: 105.9 Å
total pore volume: 0.91 ml/g
percentage of pores between 150 and 250 Å: 16.4
percentage of pores between 250 and 300 Å: 1.7
was fed, simultaneously and separately, in about 1 hour, on the one hand, with 190 g of an aqueous solution containing chromium anhydride $CrO_3$ at a concentration of 52.6% by weight, and on the other hand, with a mixture of methanol and water containing 80% by weight methanol, the alumina thus impregnated being thereafter dried in a fluid bed at 150° C. in a nitrogen stream. A quantity of 0.189 kg of dry catalyst was activated in the fluorination reactor, first at 300° C. for six hours, then at 400° C. for 24 hours, by passage of 13.5 Nl/h of an equimolecular gaseous mixture of hydrofluoric acid and 1,1,2-trichloro-1,2,2-trifluoro-ethane.

To the gaseous effluent issuing from the first reactor were added 3.8 Nl/h of fresh gaseous hexachloroacetone in order to form a mixture that was introduced into the second fluorination reactor operating at 300° C. This mixture was such that the ratio of the number of hydrofluoric acid moles introduced into the first reactor to the number of moles of halogenoacetone contained therein was 3.8:1.

The second fluorination rector was identical to the first and contained an equal quantity of the same activated catalyst as the first reactor. The flow-rate of the passage of gases in the second reactor was equal to 193 Nl/h/kg of catalyst.

The gaseous effluent issuing from the second fluorination reactor was treated in a manner known to those skilled in the art in order to separate the hexafluoroacetone produced, the chlorofluoroacetones to be recycled to the first reactor, and the unreacted hydrofluoric acid to be advantageously recycled to this same reactor.

The conversion rate of the hexachloroacetone was substantially quantitative, the yield reached 46.5 g of hexafluoroacetone/h/kg of catalyst, and the decomposition rate of the organic molecules corresponded to 0.5% of the engaged hexachloroacetone.

What is claimed is:

1. A continuous catalytic process for the preparation of hexafluoroacetone through fluorination of hexachloroacetone in the gaseous phase by anhydrous hydrofluoric acid, which comprises conducting the fluorination in two steps utilizing a catalyst comprising gamma alumina impregnated with chromium sesquioxide $Cr_2O_3$ in an amount of from 1.5 to 4 chromium atoms per liter of alumina and activated at a temperature between 300° C. and 400° C. by means of a mixture of hydrofluoric acid and 1,1,2-trichloro-1,2,2-trifluoro-ethane, the first fluorination step comprising reacting at a temperature between 330° C. and 370° C. a mixture of hydrofluoric acid and recycled products comprising chlorofluoroacetones, and the second fluorination step comprising reacting at a temperature between 280° C. and 320° C. a mixture comprising the gaseous effluent issuing from the first fluorination step and fresh hexachloroacetone in an amount whereby the ratio of the number of moles of hydrofluoric acid introduced into the first fluorination step to the number of moles of halogenoacetones introduced into the second fluorination step is between 3:1 and 5:1, the hexafluoroacetone produced being recovered from the gaseous effluent issuing from the second fluorination step and the remaining halogenoacetones being recycled to the first fluorination step.

2. The process according to claim 1, wherein the flowrate of the reactants during the first and second fluorination steps is between 150 and 200 liters per hour per kilogram of catalyst.

3. The process according to claim 2, in which the catalyst is activated by means of a mixture containing from 0.5 to 2 moles of hydrofluoric acid per mole of 1,1,2-trichloro-1,2,2-trifluoro-ethane.

4. The process according to claim 3, in which the catalyst is activated by means of a mixture containing about 1 mole of hydrofluoric acid per mole of 1,1,2-trichloro-1,2,2-trifluoro-ethane.

5. The process according to claim 1, in which the catalyst is activated by means of a mixture containing from 0.5 to 2 moles of hydrofluoric acid per mole of 1,1,2-trichloro-1,2,2-trifluoro-ethane.

6. The process according to claim 5, in which the catalyst is activated by means of a mixture containing about 1 mole of hydrofluoric acid per mole of 1,1,2-trichloro-1,2,2-trifluoro-ethane.

7. The process according to claim 6, in which the catalyst contains about 2.5 atoms of chromium per liter of alumina.

8. The process according to claim 5, in which the catalyst contains about 2.5 atoms of chromiun per liter of alumina.

9. The process according to claim 4, in which the catalyst contains about 2.5 atoms of chromium per liter of alumina.

10. The process according to claim 3, in which the catalyst contains about 2.5 atoms of chromium per liter of alumina.

11. The process according to claim 2, in which the catalyst contains about 2.5 atoms of chromium per liter of alumina.

12. The process according to claim 1, in which the catalyst contains about 2.5 atoms of chromium per liter of alumina.

* * * * *